United States Patent
Uchida

(10) Patent No.: US 8,826,369 B2
(45) Date of Patent: Sep. 2, 2014

(54) TERMINAL, COMMUNICATION SYSTEM, DATA MANAGEMENT METHOD, SERVER AND STORAGE MEDIUM

(75) Inventor: Kaoru Uchida, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 13/389,254

(22) PCT Filed: Jul. 15, 2010

(86) PCT No.: PCT/JP2010/062388
§ 371 (c)(1),
(2), (4) Date: Feb. 6, 2012

(87) PCT Pub. No.: WO2011/018937
PCT Pub. Date: Feb. 17, 2011

(65) Prior Publication Data
US 2012/0137343 A1    May 31, 2012

(30) Foreign Application Priority Data
Aug. 11, 2009 (JP) .................... 2009-186254

(51) Int. Cl.
*H04L 29/06* (2006.01)
*G06F 21/00* (2013.01)

(52) U.S. Cl.
USPC ............... 726/1; 726/26; 713/153; 713/168

(58) Field of Classification Search
None
See application file for complete search history.

(56) References Cited

U.S. PATENT DOCUMENTS

| | | | |
|---|---|---|---|
| 2004/0054918 A1* | 3/2004 | Duri et al. | 713/200 |
| 2004/0133547 A1 | 7/2004 | Doi | |
| 2005/0158767 A1* | 7/2005 | Haskell et al. | 435/6 |
| 2005/0193221 A1* | 9/2005 | Yoneyama | 713/201 |
| 2006/0265397 A1* | 11/2006 | Bryan et al. | 707/10 |
| 2009/0112872 A1 | 4/2009 | Doi | |
| 2009/0254511 A1* | 10/2009 | Yeap et al. | 707/1 |

FOREIGN PATENT DOCUMENTS

| | | |
|---|---|---|
| CN | 101108125 A | 1/2008 |
| CN | 101495030 A | 7/2009 |
| JP | 2002-207895 A | 7/2002 |
| JP | 2004-145483 A | 5/2004 |
| JP | 2005-115570 A | 4/2005 |
| JP | 2005-339308 A | 12/2005 |
| JP | 2006-085395 A | 3/2006 |
| JP | 2006-122610 A | 5/2006 |
| JP | 2008-234041 A | 10/2008 |

OTHER PUBLICATIONS

International Search Report in PCT/JP2010/062388 dated Aug. 31, 2010 (English Translation Thereof).
Chinese Office Action dated Jan. 6, 2014 (with English translation).
Japanese Office Action dated Apr. 22, 2014 with a partial English Translation.

* cited by examiner

*Primary Examiner* — Gilberto Barron, Jr.
*Assistant Examiner* — Malcolm Cribbs
(74) *Attorney, Agent, or Firm* — McGinn IP Law Group, PLLC

(57) ABSTRACT

A terminal includes an acquisition unit to acquire sensor data, a storage unit to store a policy table which defines a management policy for each sensor data or each service using the sensor data, and a control unit to acquire the management policy corresponding to the sensor data or the service with reference to the policy table and to manage the sensor data on a basis of the management policy.

10 Claims, 8 Drawing Sheets

FIG. 2

| SENSING ID | SENSOR DATA |
|---|---|

FIG. 3

| SENSING ID | USED SERVICE ID | MANAGEMENT POLICY |
|---|---|---|
| CAMERA IMAGE | FACE AUTHENTICATION | SAVING DATA IS PERMITTED ONLY IN TERMINAL. NO COMMUNICATION WITH OUTSIDE OF TERMINAL |
| CAMERA IMAGE | NETWORK ALBUM | REFERENCE BY ONESELF IS PERMITTED. NO OTHER USE |
| GPS POSITION DATA | NETWORK ALBUM | REFERENCE BY ONESELF IS PERMITTED. NO OTHER USE |
| AIR PRESSURE DATA | NETWORK WEATHER FORECAST | ANONYMIZED SENSOR DATA CAN BE PROVIDED. |
| GPS POSITION DATA | NETWORK WEATHER FORECAST | ANONYMIZED SENSOR DATA CAN BE PROVIDED. |
| PULSE DATA | HEALTH ADVICE | SENSOR DATA USING FICTITIOUS NAME CAN BE PROVIDED. |
| PEDOMETER DATA | HEALTH ADVICE | SENSOR DATA USING FICTITIOUS NAME CAN BE PROVIDED. |
| PEDOMETER DATA | WATCHING SENIOR | CRUDE SENSOR DATA INCLUDING REAL NAME CAN BE PROVIDED. |
| GPS POSITION DATA | WATCHING SENIOR | CRUDE SENSOR DATA INCLUDING REAL NAME CAN BE PROVIDED. |
| ... | | |

FIG. 4

| TERMINAL ID | SENSING ID | SENSOR DATA | USED SERVICE ID | MANAGEMENT POLICY |
|---|---|---|---|---|

FIG. 9

| SENSING ID | USED SERVICE ID | MANAGEMENT POLICY |
|---|---|---|
| GPS POSITION DATA | METABOLIC SYNDROME MANAGEMENT | ANONYMIZED SENSOR DATA CAN BE PROVIDED. |
| ACCELERATION DATA | METABOLIC SYNDROME MANAGEMENT | ANONYMIZED SENSOR DATA CAN BE PROVIDED. |
| RUNNING STEP DATA | METABOLIC SYNDROME MANAGEMENT | CRUDE SENSOR DATA INCLUDING REAL NAME CAN BE PROVIDED. |
| ... | | |

FIG. 10

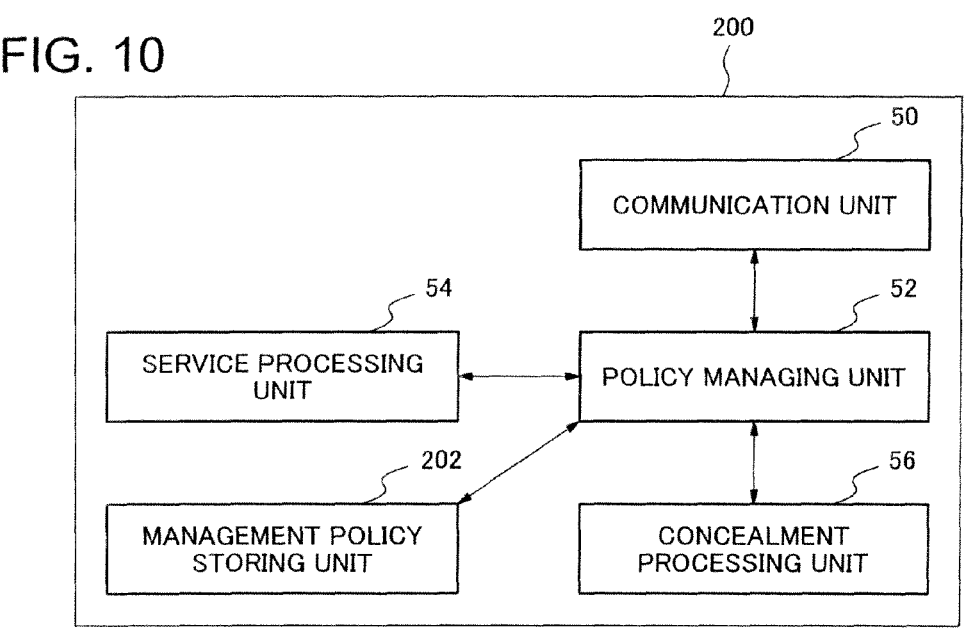

FIG. 11

| P-ID | SENSING ID | DESCRIPTION ON USED SERVICE | MANAGEMENT POLICY |
|---|---|---|---|
| 1 | CAMERA IMAGE | INCLUDING ALL | REFERENCE BY ONESELF AND BY DESIGNATED FRIEND IS PERMITTED. NO OTHER USE |
| 2 | GPS POSITION DATA | INCLUDING A WHOLE OF HEALTH CATEGORY | DATA CAN BE PROVIDED ONLY TO SERVICE BY COMPANY A. |
| 3 | ACCELERATION DATA | INCLUDING A WHOLE OF NAVIGATION CATEGORY | DATA CAN BE PROVIDED TO SERVICE B. |
| ... | | | |

FIG. 12
| TERMINAL ID | SENSING ID | POLICY ID |
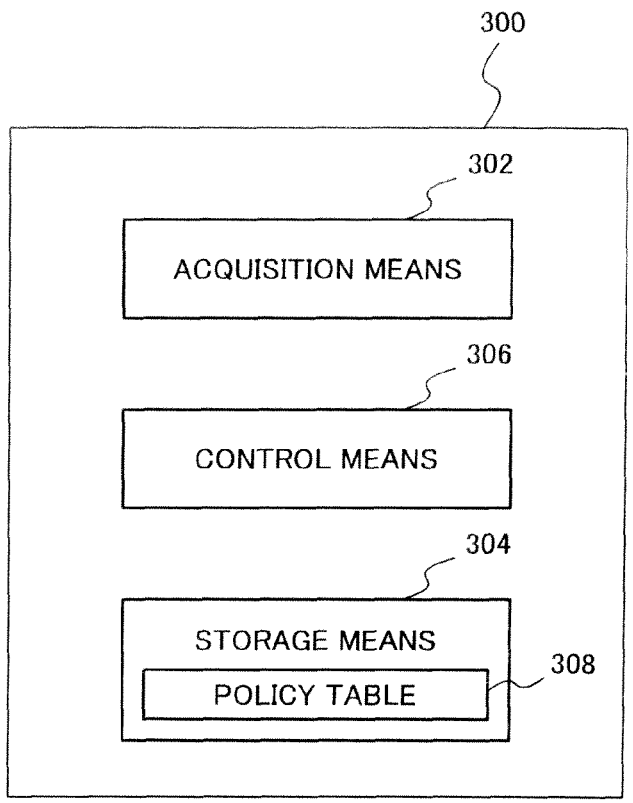
FIG. 13
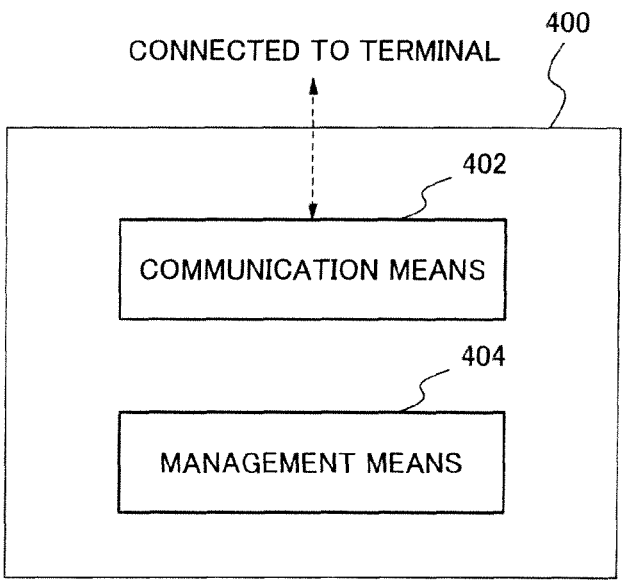
FIG. 14

TERMINAL, COMMUNICATION SYSTEM, DATA MANAGEMENT METHOD, SERVER AND STORAGE MEDIUM

TECHNICAL FIELD

The present invention relates to a terminal, a communication system a data management method, a server and a storage medium.

BACKGROUND ART

A terminal, which collects information on a state and an environment of a user by use of a built-in sensor or an external sensor connected to the terminal, and processes the information internally or sends the information to an external server, is well known. The terminal is disclosed, for example, in patent document 1.

Here, the sensor information often includes user's personal information. Accordingly, in recent years, a need for managing the information becomes increasing in order to prevent the personal information from flowing out to a malicious third person. As a method to manage the information, it is exemplified that limitation on a disclosure range is set for each information or each service.

The patent document 1 discloses an art that, in the case that user's biological information (such as blood pressure, pulse and fingerprint) is sent to a manager (corresponding to the server) by an agent (corresponding to the terminal), encryption communication is carried out after mutual authentication between the manager and the agent.

Patent document 2 discloses a service providing method which carries out control on the basis of a predetermined service rule (state of terminal, and service content corresponding to the state). The patent document 2 describes that, in the case that the terminal enters into a predetermined space (for example, art museum), a predetermined service (for example, in-house guide information) is provided.

PRECEDING TECHNICAL DOCUMENT

Patent Literature

[Patent Literature 1] Japanese Patent Application Laid-Open No. 2006-122610
[Patent Literature 2] Japanese Patent Application Laid-Open No. 2005-115570

SUMMARY OF THE INVENTION

Problem to be Solved by the Invention

Since it is usual that management of the above-mentioned sensor information, which includes the user's personal information, is left to the user, the objective and automatic management has not been carried out. The information management by the user causes a variation due to the knowledge and the ability of the user, and consequently the information management by the user has inferior reliability. Moreover, the information management by the user burdens the user severely since the user has to take care always in managing the information.

Moreover, according to the art disclosed in the patent document 1 and the patent document 2, it is difficult to manage the sensor information and result information of processing the service, which uses the sensor information, on the basis of importance, classification, personal property, a utilization form or the like. Specifically, according to the art disclosed in the patent document 1 and the patent document 2, it is difficult to carry out control that only the user is allowed to refer to his/her own sensor information, or only the sensor information which is anonymized is disclosed, or the result information which includes a real name is opened, etc.

In order to solve the above-mentioned problem, the present invention is conceived. An object of the present invention is to provide a terminal, a communication system, a data managing method, a server and a control program which can prevent certainly the personal information from flowing out without burdening the user, and manage the sensor information and the result information, which is acquired through processing the service by use of the sensor information, on the basis of the importance, the classification, the personal property, the utilization form or the like.

Solution to Problem

A terminal according to the present invention includes an acquisition means to acquire sensor data, a storage means to store a policy table which defines a management policy for each sensor data or each service using the sensor data, and a control means to acquire the management policy corresponding to the sensor data or the service with reference to the policy table and to manage the sensor data on the basis of the management policy.

A communication system according to the present invention includes a terminal and a server. The terminal includes an acquisition means to acquire sensor data, a storage means to store a policy table which defines a management policy for each sensor data or each service using the sensor data, and a control means to acquire the management policy corresponding to the sensor data or the service with reference to the policy table and to send, at least, ID (IDentifier) information which identifies the terminal, the sensor data and the management policy to the server. The server includes a management means to manage, at least, the ID and the sensor data on the basis of the management policy.

A data managing method according to the present invention manages data in a terminal and in a server. The data managing method in terminal includes storing a policy table which defines a management policy for each sensor data or each service using the sensor data, and acquiring the management policy corresponding to the sensor data or the with reference to the policy table, and managing the sensor data on the basis of the management policy, and sending, at least, ID (IDentifier) information which identifies the terminal, the sensor data and the management policy to the server. The data managing method in the server includes managing, at least, the ID information and the sensor data on the basis of the management policy.

A server according to the present invention includes a communication means to receive ID information which identifies a terminal, sensor data and a management policy for each sensor data or each service, which uses the sensor data, from the terminal, and a management means to manage, at least, the ID information and the sensor data on the basis of the management policy.

A data managing method according to the present invention manages data in a terminal. The data managing method includes storing a policy table which defines a management policy for each sensor data or each service using the sensor data, and acquiring the sensor data, and acquiring the management policy corresponding to the sensor data or the service with reference to the policy table, and managing the sensor data on the basis of the management policy.

A data managing method according to the present invention manages data in a server. The data managing method includes receiving ID information which identifies a terminal, sensor data and a management policy for each sensor data or each service, which uses the sensor data, from the terminal, and managing, at least, the ID information and the sensor data on the basis of the managing policy.

A storage medium according to the present invention stores a control program to make a computer of a terminal execute a step of storing a policy table which defines a management policy for each sensor data or each service using the sensor data, a step of acquiring the sensor data, and a step of acquiring the management policy corresponding to the sensor data or the service with reference to the policy table, and managing the sensor data on the basis of the management policy.

A storage medium according to the present invention stores a control program to make a computer of a server execute a step of receiving ID information which identifies a terminal, sensor data and a management policy for each sensor data or each service, which uses the sensor data, from the terminal, and a step of managing, at least, the ID information and the sensor data on the basis of the managing policy.

Advantageous Effect of the Invention

According to the present invention, it is possible to prevent certainly the personal information from flowing out without burdening the user, and to manage the sensor information and the result information, which is acquired through processing the service by use of the sensor information, on the basis of the importance, the classification, the personal property, the utilization form or the like.

BRIEF DESCRIPTION OF DRAWINGS

FIG. 2 shows an example of a format of first data which are sent to a sensing managing unit by a sensor interface unit a terminal shown in FIG. 1.

FIG. 3 shows an example of a format of a policy table which is stored in a management policy storing unit of the terminal shown in FIG. 1.

FIG. 4 shows an example of a format of second data which are created by the sensing managing unit in the mobile terminal shown in FIG. 1.

FIG. 9 shows an example of a format of a policy table which is stored in a management policy storing unit of the terminal shown in FIG. 8.

FIG. 10 is a block diagram showing an example of a configuration of a server according to a fourth exemplary embodiment of the present invention.

FIG. 11 shows an example of a format of a policy table which is stored in a management policy storing unit of the server shown in FIG. 10.

FIG. 12 shows an example of a format of a sensor data packet which is sent by a terminal to the server shown in FIG. 11.

FIG. 13 is a block diagram showing an example of a configuration of a terminal according to a fifth exemplary embodiment of the present invention.

FIG. 14 is a block diagram showing an example of a configuration of a server according to a sixth exemplary embodiment of the present invention.

EXEMPLARY EMBODIMENT OF PRESENT INVENTION

First Exemplary Embodiment

Figure 1:
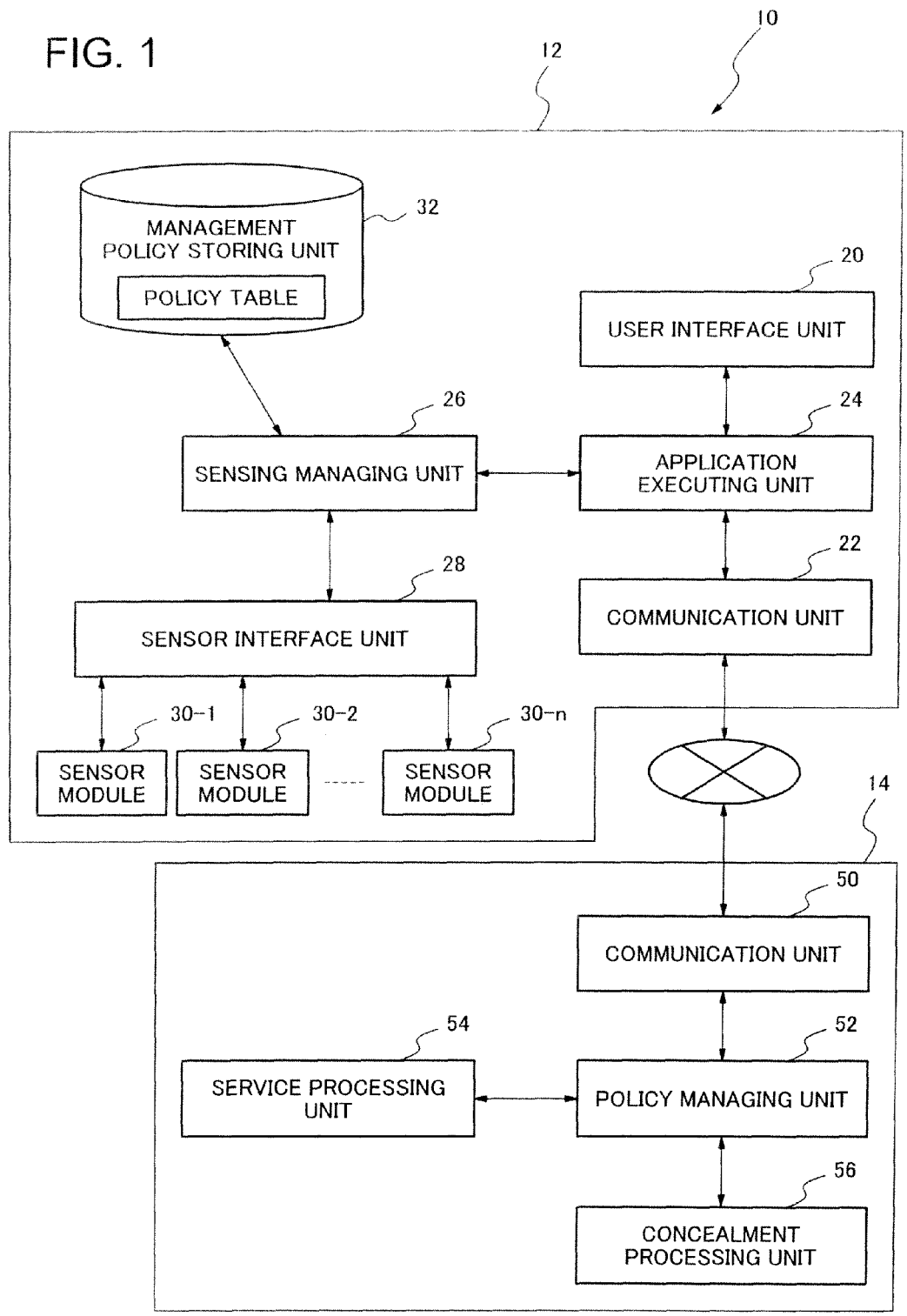
FIG. 1 is a block diagram showing an example of a configuration of a communication system according to a first exemplary embodiment of the present invention.

FIG. 1 is a block diagram showing an example of a configuration of a communication system 10 according to a first exemplary embodiment of the present invention. The communication system 10 includes a terminal and a server 14 (external apparatus). According to schematic description, the terminal 12 collects sensor data on a state and an environment of a user who carries the terminal 12, and processes the sensor data internally, or sends the sensor data to the server 14 without processing the sensor data. Meanwhile, the server 14 provides the user or another person with a predetermined service based on the sensor data which is received from the terminal 12. The terminal 12 and the server 14 are connected each other through a predetermined network.

The mobile terminal 12 includes a user interface unit 20, a communication unit 22 (communication means), an application executing unit 24 (control means), a sensing managing unit 26 and a sensor interface unit 28 (acquisition means). A management policy storing unit 32 (storage means) is connected to the sensing managing unit 26. Sensor modules 30-1 to 30-n are connected to the sensor interface unit 28.

The user interface unit 20 receives an input, which is created through the user handling a keystroke unit (not shown in the figure) such as the numerical keypad, and makes a display unit (not shown in the figure) display a service processing result which is received from the server 14. The communication unit 22 sends data to the server 14 and receives data from the server 14.

The application executing unit 24 executes a service application on a terminal side, for example, on the basis of a user's instruction issued by the user interface unit 20. The service application executed by the application executing unit 24 instructs, for example, the sensing managing unit 26 to start sensing by use of the sensor modules 30-1 to 30-n. Moreover, the service application transfers the sensor data, which is acquired from the sensing managing unit 26, to the user interface unit 20, and/or stores the sensor data in a predetermined memory (not shown in the figure). Moreover, the service application sends the sensor data, which is acquired from the sensing managing unit 26, to the server 14 via the communication unit 22. Moreover, the service application receives service processing result data, which is calculated by a server 14 side application working in cooperation with the terminal side application, from the server 14 via the communication unit 22. The service processing result data is transferred, for example, to the user interface unit 20.

The sensor interface unit 28 creates first data, which is shown in FIG. 2, on the basis of each sensor data sent from the sensor modules 30-1 to 30-n, and sends the created first data to the sensing managing unit 26. The first data includes the sensor data and a sensing ID which identifies the sensor data. For example, the sensing ID of a camera is set to 1, and that of GPS (Global Positioning System) is set to 2 or the like.

The sensor modules 30-1 to 30-n measure user's environment information and user's biological information, and sends the measured information to the sensor interface unit 28 as the sensor data. Here, a camera, GPS, an acceleration sensor, an air pressure sensor, a microphone, or a sensor which measures the blood pressure and the pulse is exemplified as the sensor modules 30-1 to 30-n.

The management policy storing unit 32 includes a policy table.

FIG. 3 shows an example of a format of the policy table which is stored in the management policy storing unit 32. In the policy table, a management policy is defined for each combination of the sensing ID and a used service ID. Here, the used service ID uses the sensor data which has the sensing ID. It may be preferable that a management policy ID instead of the management policy is used in the policy table.

For example, a face image, which is photographed with a camera in order to be used in the face authenticating application, is used only within the terminal 12, and therefore the face image is not sent to the outside (that is, to server 14). Moreover, while a camera image photographed for the network album, and its photographing location information are sent to the server 14, the camera image and its photographing location information are stored in a user's dedicated area of the server 14, and only the user can refer to the camera image and its photographing location information. Moreover, in the case that the user is provided with the network weather forecasting service, the user sends observed air pressure data and its observation location information to the server 14, but the user deletes his/her own name for concealing his/her own name when sending the data and the information. Here, the network weather forecasting service means a weather forecast service which is based on data collected from many volunteers for the network weather forecasting service and provides the volunteers with the weather forecast. Moreover, in the case of the health advice service, pulse data and pedometer data are sent to the server 14. When using the data in the server 14, a fictitious name is set and the real name is concealed so that the personal information may not flow out and may not be used for selling commodities. Here, the health advice service means a service that a user sends information on the user's health state and exercise record, and receives a medical checkup result and consultation information. Moreover, in the case of the service that a family or a watching service provider watches a solitary aged people remotely, it is unnecessary to conceal the personal information from a view point that the personal information should be disclosed publicly to provide many persons with the personal information. Accordingly, in this case, position information on an aged person who is a target for watching, and aged person's odometer data which are calculated by an analysis of acceleration information check whether the aged people falls down are sent to the server 14 without anonymizing a real name of the aged person and using a fictitious name of the aged person.

Returning to FIG. 1, the sensing managing unit 26 adds policy information to the first data on the basis of the management policy which is stored in the management policy storing unit 32. Specifically, the sensing managing unit 26 creates second data.

FIG. 4 shows an example of a format of the second data which is created by the sensing managing unit 26 in the mobile terminal 12 shown in FIG. 1. The second data includes a terminal ID which is an identifier of the terminal 12, the sensing ID, the sensor data, the used service ID and the management policy. The sensing managing unit 26 sends the created second data to the application executing unit 24. In the case that there are plural sensor data each of which has the same used service ID, it is possible to make the second data embedded in one packet which includes a plurality of the sensor data. For example, in the case of the network weather forecast shown in FIG. 3, it is possible to make the second data embedded in one packet which includes the air pressure data and the GPS position data. Or, it is also possible to make the second data embedded in a plurality of packets each of which is separated per the sensor data. For example, in the case of the network weather forecast, it is possible to make the second data embedded in two packets one of which includes the air pressure data and the other of which includes the GPS position data. The application executing unit 24 (service application) checks the management policy of the second data, and judges whether the management policy prescribes that the process should be carried out only within the terminal 12 or the management policy prescribes that the second data should be sent to the server 14. In the case that the management policy prescribes that the second data should be sent to the server 14, the application executing unit 24 sends the second data to the server 14 via the communication unit 22. On the other hand, in the case that the management policy prescribes that the process should be carried out only within the terminal 12, the application executing unit 24 transfers the sensor data, which is included in the second data, to the user interface unit 20. Or, the application executing unit 24 stores the sensor data, which is included in the second data, in a predetermined memory (not shown in the figure).

Meanwhile, the server 14 includes a communication unit 50 (communication means), a policy managing unit 52 (management means), a service processing unit 54 and a concealment processing unit 56. The communication unit 50 sends data to the mobile terminal 12 and receives data from the mobile terminal 12. The policy managing unit 52 refers to the management policy of the second data which is received from the terminal 12 via the communication unit 50, and carries out data processing on the basis of the management policy. Specifically, in the case that the management policy prescribes a concealing process such as anonymizing the real name and using the fictitious name, the policy managing unit 52 carries out a process of anonymizing the real name or a process of using the fictitious name for the second data, and afterward sends the processed second data to the service processing unit 54. On the other hand, in the case that the management policy prescribes that it is possible to provide data with using the real name, the policy management unit 52 does not carry out any process for the second data and sends the second data to the service processing unit 54 as it is. Moreover, the policy managing unit 52 receives provided information from the service processing unit 54 as a result of a service process which is carried by the service processing unit 54 on the basis of the sensor data supplied by the policy managing unit 52. Afterward, the policy managing unit 52 sends the provided information, which is received from the service processing unit 54, to the terminal 12 via the communication unit 50.

The service processing unit 54 processes a predetermined service on the basis of the second data which is received from the policy managing unit 52. Here, the predetermined service means a service which is indicated by the used service ID shown in FIG. 3. As a specific example of the service, the network album service and the network weather forecast service are exemplified. The service processing unit 54 sends the provided information to the policy managing unit 52 as the result of the service process.

The concealment processing unit 56 carries out the concealing process for the second data which is received from the policy managing unit 52. Here, the concealing process means a process to conceal a terminal corresponding to a data source. The concealment processing unit 56 sends the second data, for which the concealing process is carried out, to the policy managing unit 52. Here, in the case that it is necessary to anonymize the real name, the concealment processing unit 56 deletes the terminal ID of the second data. Moreover, in the case that it is necessary to use the fictitious name, the concealment processing unit 56 converts the terminal ID of the second data into a unique virtual ID.

Figure 5:
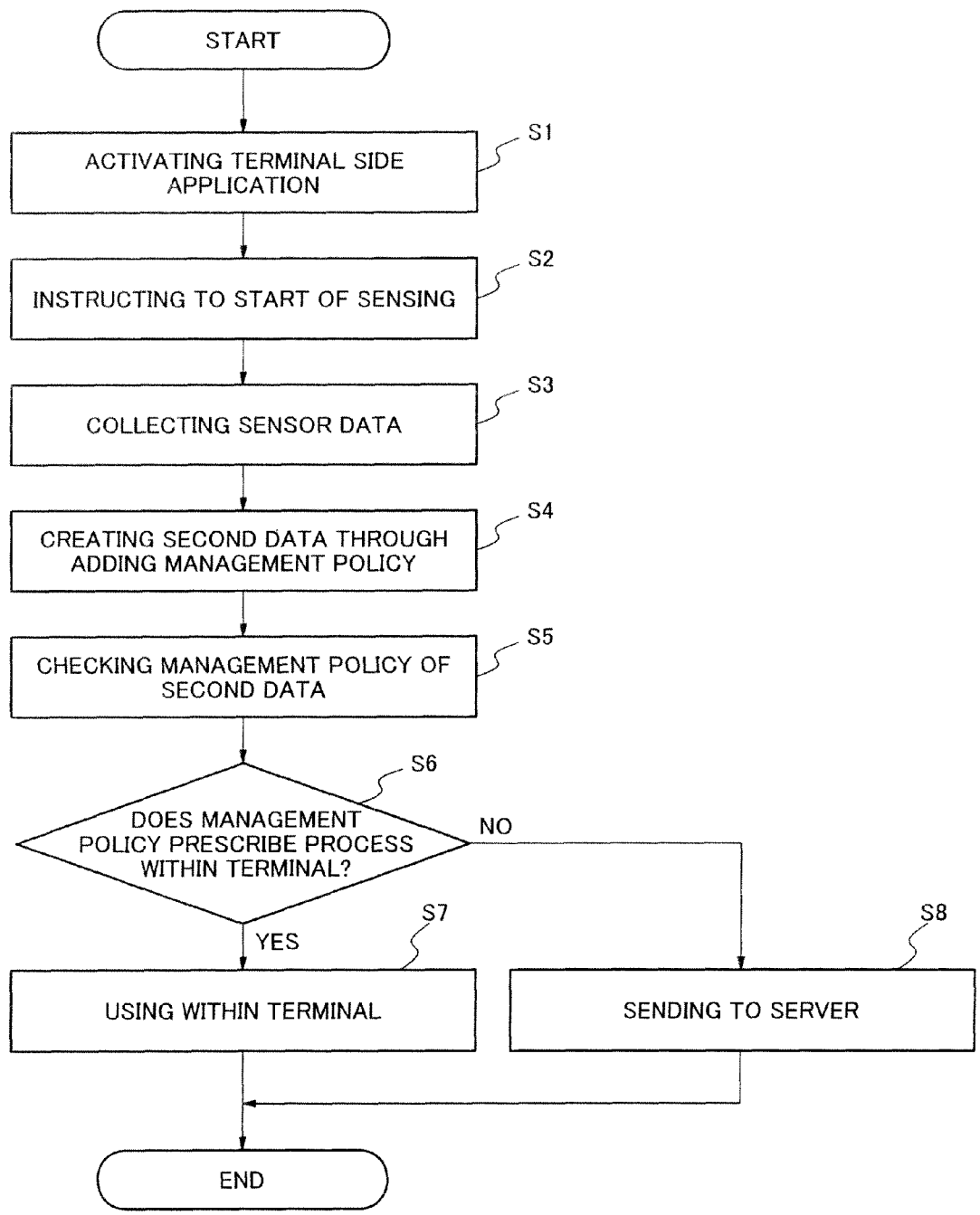
FIG. 5 is a flowchart showing an example of an operation of the terminal shown in FIG. 1.

FIG. 5 is a flowchart showing an example of an operation of the terminal 12 shown in FIG. 1.

The application executing unit 24 activates a predetermined service application (for example, network weather forecast application), for example, on the basis of a user's instruction which is inputted from the user interface unit 20 (Step S1). The service application executed by the application executing unit 24 instructs the sensing managing unit 26 to start sensing by use of the sensor modules 30-1 to 30-*n* (Step S2). The sensor modules 30-1 to 30-*n* measure the user's environment information and the user's biological information (in the case of the network weather forecast, air pressure data and its observation location information), and sends the measured information to the sensor interface unit 28 as the sensor data (Step S3).

The sensor interface unit 28 creates the first data (refer to FIG. 2) on the basis of each sensor data sent from the sensor modules 30-1 to 30-*n* and sends the first data to the sensing managing unit 26. The sensing managing unit 26 adds the policy information to the first data on the basis of the management policy which is stored in the management policy storing unit 32, and creates the second data (refer to FIG. 4) (Step S4). The sensing managing unit 26 sends the created second data to the application executing unit 24. Here, a packet, which includes the sent second data, may include both of two sensor information (air pressure data and its observation location information) or packets may be made for each of the sensor information.

The application executing unit 24 (service application) checks the management policy of the second data (Step S5). A case that the management policy of the second data prescribes that the process should be carried out only within the terminal 12 (Yes in Step S6) will be described in the following. In this case, the application executing unit 24 does not send the second data to the server 14. The sensor data included in the second data is used only within the terminal 12 (Step S7). For example, the application processing unit 24 transfers the sensor data to the user interface unit 20 and makes a display unit display the sensor data, or stores the sensor data in a memory of the terminal 12.

On the other hand, in the case that the management policy prescribes that the second data should be sent to the server 14 (No in Step S6), the application executing unit 24 sends the second data to the server 14 via the communication unit 22 (Step S8).

Figure 6:
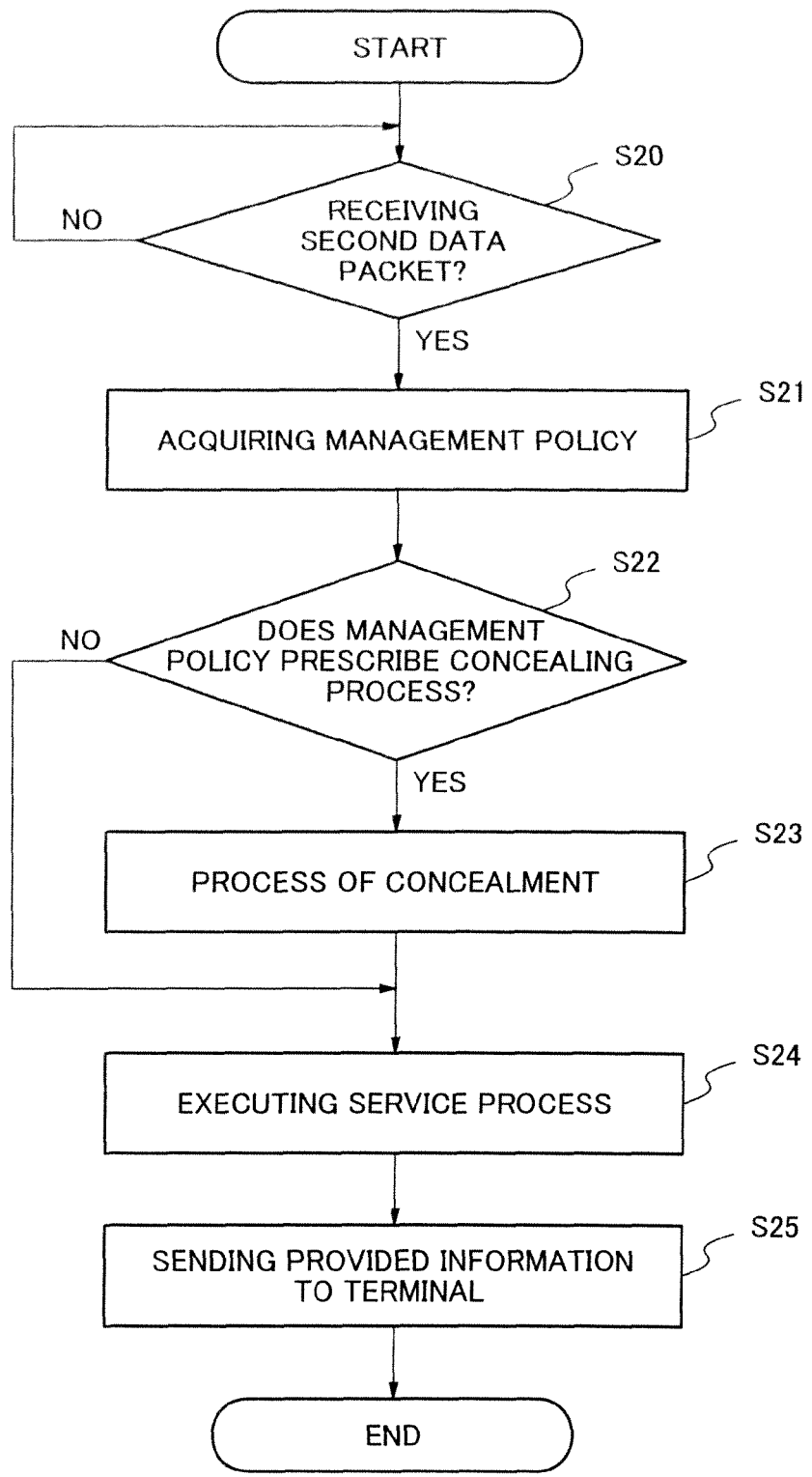
FIG. 6 is a flowchart showing an example of an operation of a server shown in FIG. 1.

FIG. 6 is a flowchart showing an example of an operation of the server 14 shown in FIG. 1.

The communication unit 50 checks whether the packet including the second data is received from the terminal 12 (Step S20). In the case that the second data packet is not received (No in Step S20), the communication unit 50 checks again whether the second data packet is received. In the case that the second data packet is received (Yes in Step S20), the policy managing unit 52 acquires the management policy of the received second data packet (Step S21). The policy managing unit 52 checks whether the management policy prescribes the concealing process such as the process of anonymizing the real name or the process of using the fictitious name (Step S22).

In the case that the management policy prescribes the concealing process (Yes in Step S22), the policy managing unit 52 carries out the concealing process for the second data (Step S23). Specifically, the policy managing unit 52 sends the second data to the concealment processing unit 56. The concealment processing unit 56 carries out the predetermined concealing process for the second data which is received from the policy managing unit 52. Here, for example, in the case that it is necessary to anonymize the real name, the concealment processing unit 56 deletes the terminal ID of the second data. Moreover, in the case that it is necessary to use the fictitious name, the concealment processing unit 56 converts the terminal ID of the second data into an unique virtual ID. The concealment processing unit 56 sends the second data, for which the concealing process is carried out, to the policy managing unit 52. The second data, for which the concealing process has been completed, is sent to the service processing unit 54 by the policy managing unit 52. The service processing unit 54 carries out a predetermined service (for example, network weather forecast service) process based on the second data which is received from the policy managing unit 52 (Step S24). The policy managing unit 52 sends the provided information, which is acquired from the service processing unit 54 as the result of the service process carried by the service processing unit 54, to the terminal 12 which supplies the sensor data, or to another apparatus (Step S25). Here, as an example of "the provided information which is acquired as the result of the service process", a weather forecast result of the network weather forecast service is exemplified. Moreover, as an example of "another apparatus", a terminal held by the family or the watching service provider is exemplified. Here, it is possible that provided information is restored to the original terminal ID only when the provided information is sent to the terminal 12 which supplies the sensor data.

On the other hand, in the case that the management policy does not prescribe the concealing process (No in Step S22), the concealing process (process in Step S23) for the second data is skipped. That is, the policy managing unit 52 provides the service processing unit 54 with the second data, which is received from the terminal apparatus 12, as it is.

As described above, according to the first exemplary embodiment, the management policy is determined for each sensor data or each service application, and the terminal 12 and the server 14 manage the information on the basis of the management policy. Here, the management policy can prescribe a range where the information can be used (for example, the information can be used only within the terminal 12, or the information is sent to the server 14 on the condition that the information is stored in an area where only the user can access). Moreover, it is possible to determine, as the management policy, whether the personal information is concealed (for example, anonymizing the real name or using the fictitious name) or not.

That is, according to the first exemplary embodiment, it is possible to manage the sensor information and the result information, which is acquired through processing the service by use of the sensor information, on the basis of the importance, the classification, the personal property, the utilization form or the like.

Furthermore, the management policy is stored in the management policy storing unit 32 in advance before the process. As mentioned above, the information managing process in the terminal 12 and the server 14 is carried out automatically on the basis of the management policy. Accordingly, it is possible to carry out the information management more objectively and more automatically than manual management based on user's discretion. That is, there is no case that variation in the precision of the information management is caused due to the user's knowledge and ability. Accordingly, it is possible to prevent surely the personal information from flowing out without burdening the user.

Here, while the case that the sensor modules 30-1 to 30-*n* are mounted within the terminal 12 is exemplified according to the first exemplary embodiment described above, it may be preferable that the sensor modules 30-1 to 30-*n* are arranged outside the terminal 12. In this case, the sensor modules 30-1 to 30-*n* are connected to the sensor interface unit 28, for example, via a cable and a connector. Or, the sensor modules 30-1 to 30-*n* are connected through the air to the sensor interface unit 28 by use of a predetermined short distance radio system (for example, Bluetooth and Wi-Fi (Wireless Fidelity)).

Moreover, while the case that the service application of the terminal 12 is activated by the user's manual handling is exemplified according to the first exemplary embodiment described above, a method to activate the application is not limited to the above method. For example, it is possible to activate the application automatically on the basis of a time counting result by a timer (not shown in the figure it is also possible to activate the application on the basis of an instruction issued by the server 14.

Moreover, it may be preferable that the application is stored in a storage unit (not shown in the figure) of the terminal 12 in advance, or it may be preferable that the application is downloaded from the server 14 at a predetermined timing.

Moreover, while the case that the provided information, which is acquired as the result of the service process, is sent back to the terminal 12 which supplies the sensor data is exemplified according to the first exemplary embodiment described above, a destination of the provided information is not limited to the terminal 12. For example, in the case of the watching service, the provided information may be sent to a family other than a person of the family who is a contractor of the watching service. Moreover, the provided information is used in cooperation with other network services.

Second Exemplary Embodiment

Figure 7:
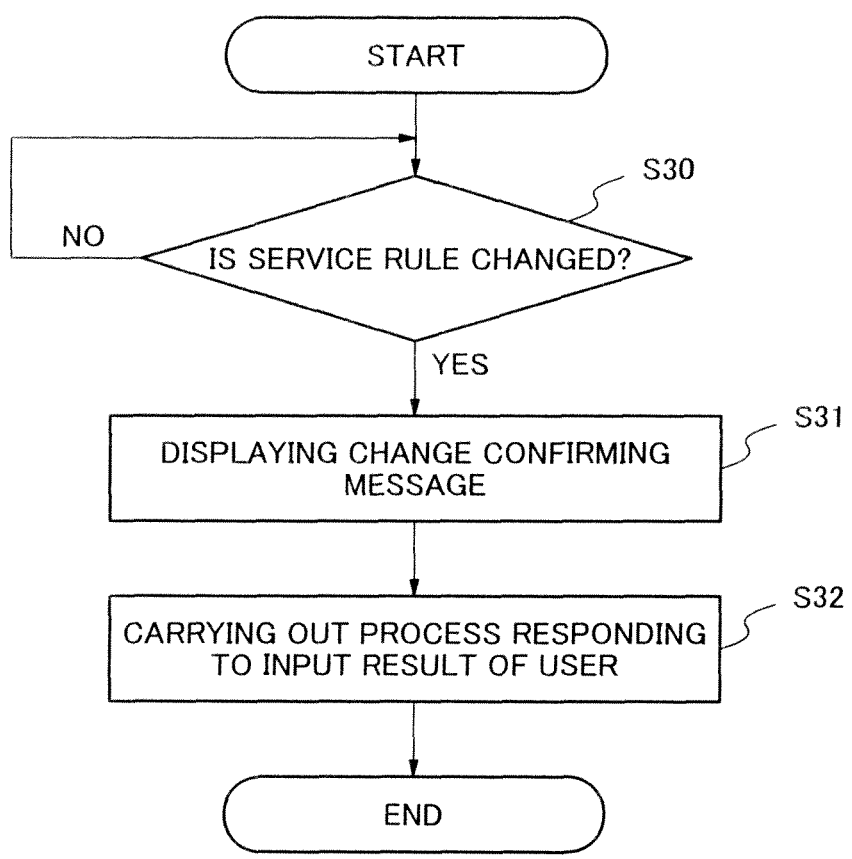
FIG. 7 is a flowchart showing an example of an operation of a terminal according to a second exemplary embodiment of the present invention.

FIG. 7 is a flowchart showing an example of an operation of a terminal according to a second exemplary embodiment of the present invention. According to the present exemplary embodiment, a configuration of the terminal is the same as one of the terminal 12 according to the first exemplary embodiment. Therefore, description on the configuration is omitted. On the other hand, an operation of the terminal is different from one according to the first exemplary embodiment. Accordingly, only the different point will be described in the following.

Through the application executing unit 24 checking whether a notification from the server 14 exists or not, the application executing unit 24 judges whether a service rule is changed or not (Step S30). In the case that the service rule is changed (Yes in Step S30), the application executing unit 24 makes a display unit of the user interface unit 20 display a change confirming message (Step S31). Here, describing specifically, it is assumed, for example, that a specification of the network album service is expanded so that the family and the friend, who are designated in advance, may be permitted to see a group of specific photographs. In this case, the application executing unit 24 makes the display part of the user interface unit 20 display the confirming message such as "Do you change the policy and do you expand a disclosure range up to your family and your friend?" Then, the application executing unit 24 carries out a process corresponding to an user's input which responds to the change confirming message (Step S32). Specifically, in the case that the user's response to the confirming message is, for example, "no change", the application managing unit 24 does not change the management policy. On the other hand, in the case that the user's response to the confirming message is, for example, "I change the policy only this time." or "I change the policy so that the changed policy may be applicable always in this service", the application managing unit 24 changes the management policy.

According to the second exemplary embodiment, since the change of the service rule can be reflected at any time in the management policy as described above, it is possible to carry out more flexible information management. Furthermore, in the case, since it is confirmed whether the user permits the change, it is possible to manage the information more surely.

Third Exemplary Embodiment

Figure 8:
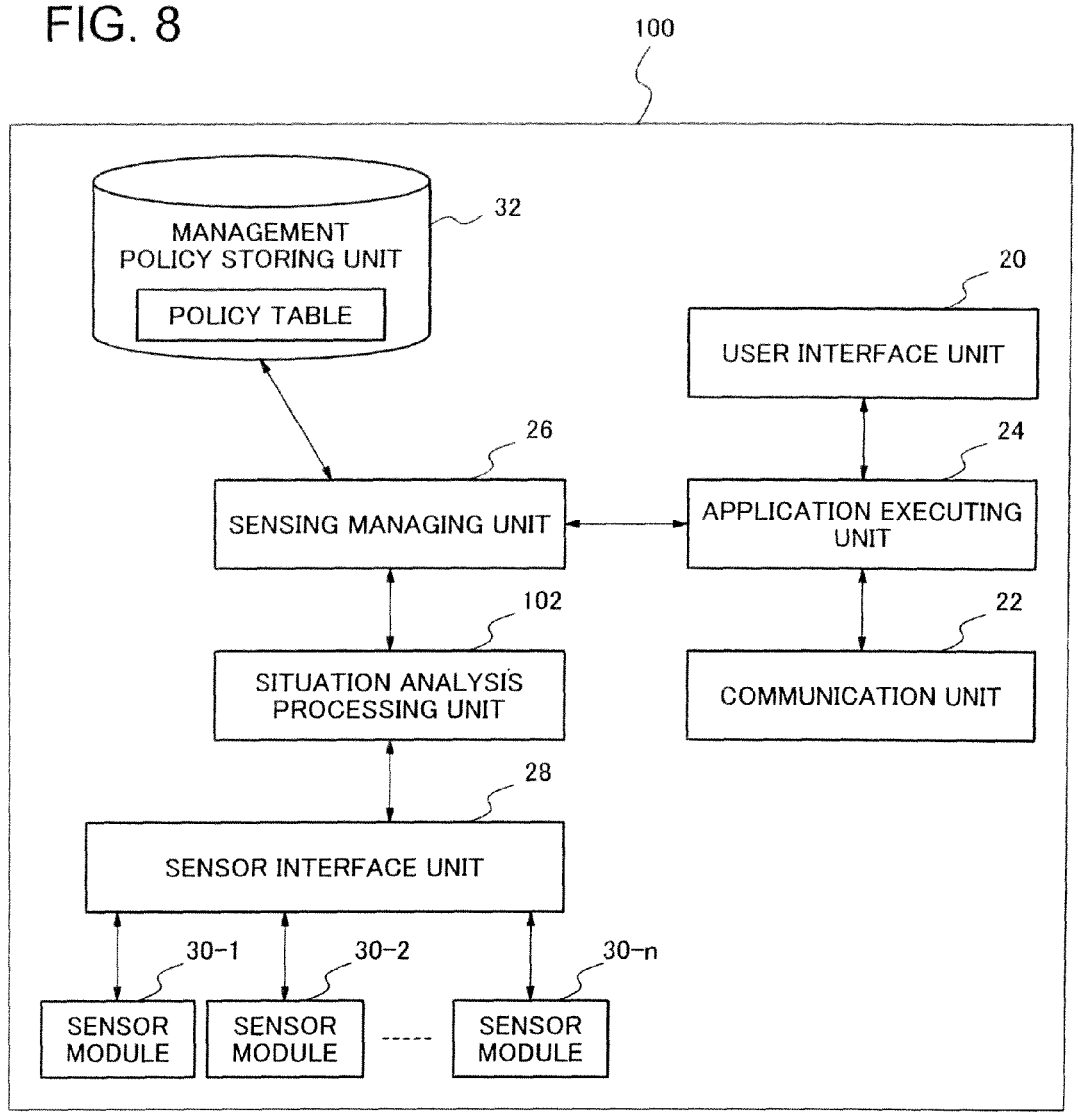
FIG. 8 is a block diagram showing an example of a configuration of a terminal according to a third exemplary embodiment of the present invention.

FIG. 8 is a block diagram showing an example of a configuration of a terminal 100 according to a third exemplary embodiment of the present invention. The terminal 100 is different from the terminal 12 shown in FIG. 1 in a point that the terminal 100 includes a situation analysis processing unit 102. Therefore, since the other constituents are the same as ones of the terminal 12, description on the other constituents is omitted.

Incidentally, it is possible to assume a case that a sensing using service uses not only the sensor data as it is, but also a result of processing a combination of the sensor data. For example, it is possible to assume a service which estimates whether the user stays in a home, or walks, or runs, or rides on a vehicle such as a bus or a train through analyzing a combination of output data of GPS, an acceleration sensor and a microphone.

The situation analysis processing unit 102 is corresponding to the service. That is, the situation analysis processing unit 102 judges by use of a plurality of sensor data. The situation analysis processing unit 102 sends the judgment result to the sensing managing unit 26 as the first data (refer to FIG. 2) similarly to the case of the crude sensor data. For example, in the case of estimating "running step data" on the basis of "position data" and "acceleration data", the sensing ID is the "running step data".

FIG. 9 is an example of a format of a policy table stored in a management policy storing unit 30 of the terminal 100 according to the third exemplary embodiment. Each data (GPS position data and acceleration data which are crude, and running step data which is the result data of the process) is managed based on each management policy shown in FIG. 9. In this case, the running step data, which is the result data of the process, is disclosed with the real name. On the other hand, data such as the GPS position data and the acceleration data, which are crude, is provided but is anonymized so that the user may not be identified.

As described above, through applying the information management, which is based on the management policy, also to the calculation result data which is calculated on the basis of plural sensor data, it is possible to carry out more precise information management control. Furthermore, it is possible to carry out more flexible information management which can respond to user's needs. Specifically, it is possible that the crude data is concealed since the data has a possibility to identify the user while the "result data" is disclosed with the user's real name.

Fourth Exemplary Embodiment

FIG. 10 is a block diagram showing an example of a configuration of a server 200 according to a fourth exemplary embodiment of the present invention. The terminal 100 is different from the server 14 shown in FIG. 1 in a point that the terminal 100 includes a management policy storing unit 202 furthermore. Therefore, since the other constituents are the same as ones of the terminal 14, description on the other constituents is omitted.

FIG. 11 is an example of a format of a policy table which is stored in the management policy storing unit 202. That is, the policy table shown in FIG. 11 which is prepared by use of appropriate description, is sent to the server 200 in advance or at every time when a change at the terminal side is generated, and then the server 200 manages the sent policy table. Here, P-ID means a policy ID.

FIG. 12 is an example of a format of a sensor data packet which is sent to the server 200 by the terminal 12. The sensor data packet includes the policy ID.

According to the fourth exemplary embodiment described above, the server 200 refers to the policy table which is shared with the terminal 12, and manages the policy table. Accordingly, it is possible to carry out more precise information management. Furthermore, it is possible to restrain an amount of communication data exchanged between the terminal 12 and the server 200 since the server 200 includes the common policy table.

Fifth Exemplary Embodiment

FIG. 13 is a block diagram showing an example of configuration of a terminal 300 according to a fifth exemplary embodiment of the present invention. The terminal 300 includes an acquisition means 302, a storage means 304 and a control means 306. The acquisition means 302 acquires sensor data. The storage means 304 stores a policy table 308 which defines a management policy for each sensor data or each service using the sensor data. The control means 306 acquires the management policy corresponding to the sensor data or the service with reference to the policy table 308, and manages the sensor data on the basis of the management policy.

As described above, according to the fifth exemplary embodiment, management policy is determined for each sensor data or each service application, and then the terminal 300 manages the information on the basis of the management policy. Here, as the management policy, it is possible to prescribe, for example, a range where the information can be used. For example, it is possible to prescribe that the information must be used only within the terminal 300, or the information must be stored in an area where only the user can access while the information is sent to an external apparatus (for example, server).

That is, according to the fifth exemplary embodiment, it is possible to manage the sensor information and the result information, which is acquired through processing the service by use of the sensor information, on the basis of the importance, the classification, the personal property, the utilization form or the like.

Furthermore, the management policy is stored in the storage means 304 in advance before the process. As mentioned above, the information management process in the terminal 300 is carried out automatically on the basis of the management policy. Accordingly, it is possible to carry out the information management more objectively and more automatically than manual management based on user's discretion. That is, there is no case that variation in the precision of the information management is caused due to the user's knowledge and ability. Accordingly, it is possible to prevent surely the personal information from flowing out without burdening the user.

Sixth Exemplary Embodiment

FIG. 14 is a block diagram showing an example of a configuration of a server 400 according to a sixth exemplary embodiment of the present invention. The server 400 includes a communication means 402 and a management means 404. The communication means 402 receives ID information which identifies a terminal (not shown in the figure), sensor data, and a management policy for each sensor data or each service, which uses the sensor data, from the terminal. The management means 404 manages, at least, the ID information and the sensor data on the basis of the management policy.

As described above, according to the sixth exemplary embodiment, the management policy is determined for each sensor data or each service application, and then the server 400 manages information on the basis of the management policy. Here, it is possible to determine, as the management policy, for example, whether personal information is concealed (for example, anonymizing a real name or using a fictitious name) or not.

That is, according to the sixth exemplary embodiment, it is possible to manage sensor information and result information which is acquired through processing the service by use of the sensor information, on the basis of the importance, the classification, the personal property, the utilization form or the like.

Furthermore, the management policy is included in the data received from the terminal. As mentioned above, information management process in the server 400 is carried out automatically on the basis of the management policy. Accordingly, it is possible to carry out the information management more objectively and more automatically than manual management based on user's discretion. That is, there is no case that variation in the precision of the information management is caused due to the user's knowledge and ability. Accordingly, it is possible to prevent surely the personal information from flowing out without burdening the user.

Here, it is described in the first to the sixth exemplary embodiments that the terminal (12, 100 and 300) and the server (14, 200 and 400) are controlled by dedicated hardware. However, the terminal and the server may be controlled by a computer circuit (for example, CPU (Central Processing Unit)), which is not shown in the figure, and operate on the basis of a control program. In this case, the control program is stored in a storage media (for example, ROM (Read Only Memory) and a hard disk) in the terminal and the server or an external storage media (for example, a removable media and a removable disk), and the control program is read and executed by the above-mentioned computer circuit.

Moreover, according to the first to the sixth exemplary embodiments, it may be preferable that the network between the terminal and the server is wired or wireless.

While the invention has been particularly shown and described with reference to exemplary embodiments thereof, the invention is not limited to these embodiments. It will be understood by those of ordinary skill in the art that various changes in form and details may be made therein without departing from the spirit and scope of the present invention as defined by the claims.

This application is based upon and claims the benefit of priority from Japanese Patent Application No. 2009-186254, filed on Aug. 11, 2009, the disclosure of which is incorporated herein in its entirety by reference.

DESCRIPTION OF THE CODES

- 10 Communication system
- 12, 100 and 300 Terminal
- 14, 200 and 400 Server
- 20 User interface unit
- 22 Communication unit
- 24 Application executing unit
- 26 Sensing managing unit
- 28 Sensor interface unit
- 30-1 to 30-$n$ Sensor module
- 32 Management policy storing unit
- 50 Communication unit
- 52 Policy managing unit
- 54 Service processing unit
- 56 Concealment processing unit
- 102 Information analysis processing part
- 202 Management policy storing unit
- 302 Acquisition means
- 304 Storage means
- 306 Control means
- 308 Policy table
- 402 Communication means
- 404 Management means

The invention claimed is:

1. A communication system which comprises:
   a terminal of a user; and
   a server which processes a predetermined service on a basis of sensor data,
   wherein the terminal comprises:
   a sensor interface unit to acquire the sensor data including user's environment information and user's biological information;
   a management policy storing unit to store a policy table including a management policy which defines utilization form of the sensor data including concealment rules of a terminal identifier of a data source according to a combination of sensor data and a service using the sensor data;
   a sensing management unit to acquire the management policy corresponding to the combination of the sensor data and the service with reference to the policy table; and
   an application execution unit to process the sensor data only within the terminal when the utilization form of the sensor data defined by the management policy specifies to process the sensor data only within the terminal, and to send, at least, ID (IDentifier) information which identifies the terminal, the sensor data, and the management policy to the server when the utilization form of the sensor data defined by the management policy specifies to process the sensor data in the server, and
   wherein the server comprises:
   a policy management unit that carries out a concealing process which conceals the ID information corresponding to a data source of the sensor data on a basis of the concealment rules in the management policy; and
   a service processing unit that processes the predetermined service on a basis of the sensor data and the ID information to which the concealing process has been applied.

2. The communication system according to claim 1, wherein the server further comprises:
   a concealment processing unit to carry out the concealing process for the ID information according to the concealment rules by deleting the ID information when anonymizing a real name is needed, and by replacing the ID information with a virtual ID information when using a fictitious name is needed.

3. The communication system according to claim 1, wherein the application executing unit receives a notification of a change of a service rule from the server, and reflects the change to the management policy which relates to the service rule according to a user intention to the change in the management policy.

4. The communication system according to claim 1, wherein the server further comprises a second management policy storing unit which shares the policy table with the terminal, and
   wherein the terminal sends the policy table to the server in advance or at every time when a change at a terminal side is generated, and the policy management unit manages, at least, the ID information and the sensor data on a basis of the policy table.

5. A data managing method in a communication system which comprises a terminal of a user and a server which processes a predetermined service on a basis of sensor data, said data management method comprising:
   storing a policy table including a management policy which defines utilization form of the sensor data including concealment rules of a terminal identifier of a data source according to a combination of the sensor data and a service which uses the sensor data in the terminal;
   acquiring the sensor data including user's environment information and user's biological information in the terminal;
   acquiring the management policy corresponding to the combination of the sensor data and the service with reference to the policy table in the terminal;
   processing the sensor data on a basis of the management policy in the terminal when the utilization form of the sensor data defined by the management policy specifies to process the sensor data only within the terminal;
   sending, at least, ID information which identifies the terminal, the sensor data, and the management policy to the server when the utilization form of the sensor data defined by the management policy specifies to process the sensor data in the server;
   carrying out a concealing process which conceals the ID information corresponding to a data source of the sensor data on a basis of the concealment rules in the management policy in the server; and
   processing the predetermined service in the server on a basis of the sensor data and the ID information to which the concealing process has been applied.

6. The communication system according to claim 1, wherein the terminal further comprises:
   a situation analysis processing unit which analyzes a combination of a plurality of sensor data for a service which uses the analyzing result, and outputs an analyzing result together with a plurality of crude sensor data having been analyzed, and
   wherein a concealment rule of the ID information is defined differently for each of the analyzing result and the plurality of crude sensor data even in a same service.

7. The data managing method according to claim 5, wherein said carrying out concealing process comprises:
   carrying out the concealing process for the ID information according to the concealment rules by deleting the ID information when anonymizing a real name is needed, and by replacing the ID information with a virtual ID information when using a fictitious name is needed.

8. The data managing method according to claim 5, further comprising:
receiving a notification of a change of a service rule from the server, and reflecting the change to the management policy which relates to the service rule according to a user intention to the change in the management policy in the terminal.

9. The data managing method according to claim 5, further comprising:
providing the policy table in the server for sharing with the terminal;
sending the policy table from the terminal to the server in advance or at every time when a change at the terminal side is generated; and
managing, at least, the ID information and the sensor data on a basis of the policy table.

10. The data managing method according to claim 5, further comprising:
analyzing a combination of plurality of sensor data for a service which uses the analyzing result; and
outputting an analyzing result together with a plurality of crude sensor data having been analyzed,
wherein the concealment rule of the ID information is defined differently for each of the analyzing result and the plurality of crude sensor data even in a same service.

* * * * *